(12) United States Patent
Liu et al.

(10) Patent No.: US 6,582,574 B1
(45) Date of Patent: Jun. 24, 2003

(54) PK-MATCHED RUNNING BUFFERS FOR GEL ELECTROPHORESIS

(75) Inventors: Qiang Liu, Upland, CA (US); Steve S. Sommer, Duarte, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/536,392

(22) Filed: Mar. 28, 2000

Related U.S. Application Data

(60) Provisional application No. 60/127,087, filed on Mar. 31, 1999.

(51) Int. Cl.$^7$ .......................... B01D 57/02; C09K 3/00; C07K 1/26; G01N 27/447
(52) U.S. Cl. ..................... 204/456; 252/189; 204/461; 435/967; 436/18
(58) Field of Search .................. 252/189; 435/967; 436/18; 204/456, 461

(56) References Cited

U.S. PATENT DOCUMENTS

| | | | | |
|---|---|---|---|---|
| 5,174,872 A | * | 12/1992 | Scott | 436/18 X |
| 5,227,305 A | * | 7/1993 | Manzoni et al. | 436/18 X |
| 5,284,771 A | * | 2/1994 | Fan et al. | 436/18 X |
| 5,651,876 A | * | 7/1997 | West et al. | 436/18 X |
| 5,998,216 A | * | 12/1999 | O'Donnell | 436/18 X |
| 6,056,920 A | * | 5/2000 | Lepre | 436/18 X |

OTHER PUBLICATIONS

Voytas, D., et al., "Current Protocols in Molecular Biology," (1988), pp. 2.5.1–2.5.9.

Sambrook, J., et al., "Molecular Cloning: A Laboratory Manual," *Cold Spring Laboratory Press,*, (1989), pp. 6.1–6.62.

McDonnel, M. et al., "Analysis of Restriction Fragments of T7 DNA and Determination of Molecular Weights by Electrophoresis in Neutral and Alkaline Gels," *J. Mol. Biol.*, (1977), vol. 110, pp. 119–146.

Southern, E., "Gel Electrophoresis of Restriction Fragments," *Methods in Enzymology*, (1979), vol. 68, pp. 152–176.

Schwartz, D., et al., "Separation of Yeast Chromosome–Sized DNAs by Pulsed Field Grad ient Gel Electrophoresis," *Cell*, (1984), vol. 37, pp. 67–75.

Sanger, F., et al., "DNA sequencing with Chain–terminating Inhibitors," *Proc. Natl. Acad. Sci. U.S.A.*, (1977), vol. 74, No. 12, pp. 5463–5467.

Innis, M., et al., "DNA Sequencing with *Thermus aquaticus* DNA polymerase and Direct Sequencing of Polymerase Chain Reaction–Amplified DNA," *Proc. Natl. Acad. Sci. U.S.A.*, (1988), vol. 85, pp. 9436–9440.

Orita, M. et al. "Detection of Polymorphisms of Human DNA by Gel Electrophoresis as Single–strand Conformation Polymorphisms," *Proc. Natl. Acad. Sci. USA*, (1989), vol. 86, pp. 2766–2770.

Sarkar, G., et al., "Dideoxy Fingerprinting (ddF): A Rapid and Efficient Screen for the Presence of Mutations," *Genomics*, (1992), vol. 13, pp. 441–443.

Liu, Q., et al., "Restriction Endonuclease Fingerprinting (REF): A Sensitive Method for Screening Mutations n Long, Contiguous Segments of DNA," *BioTechniques*, (1995), vol. 18, pp. 470–477.

Kuhn, R., et al., "Capillary Electrophoresis: Principles and Practice," (1993), pp. 37–101.

Yoshitake, S., et al., "Nucleotide Sequence of the Gene for Human Factor IX (Antihemophilic Factor B)," *Biochemistry*, (1985), vol. 24, pp. 3736–3750.

Sarkar, G., et al., "Access to a Messenger RNA Sequence or Its Protein Product is not Limited by Tissue or Species Specificity," *Science*, (1989), vol. 244, pp. 331–334.

Liu, Q., et al., "Parameters Affecting the Sensitivities of Dideoxy Fingerprinting and SSCP," *PCR Methods and Applications*, (1994), vol. 4 pp. 97–108.

Helling, R., et al., "Analysis of Endonuclease R–EcoRI Fragments of DNA from Lambdoid Bacteriophages and Other Viruses by Agarose–Gel Electrophoresis," *Journal of Virology*, (1974), vol. 14, pp. 1235–1244.

Yarmola, E., et al., "The Relative Contributions of Dispersion and Diffusion to Band Spreading (resolution) in Gel Electrophoresis," *Electrophoresis*, (1996), vol. 17, pp. 1416–1419.

Good, N., et al., "Hydrogen Ion Buffers for Biological Research," *Biochemistry*, (1966), vol. 5, No. 2, pp. 467–477.

Stoll, V., et al., "Buffers: Principles and Practice," *Methods Enzymol.*, (1990), vol. 182, pp. 24–38.

Ellis, K., et al., "Buffers of Constant Ionic Strength for Studying pH–Dependent Processes," *Methods of Enzymol.*, (1982), vol. 87, pp. 405–426.

Ganguly, A., et al., "Conformation–sensitive Gel Electrophoresis for Rapid Detection of Single–base Differences in Double–stranded PCR Products and DNA Fragments: Evidence for Solvent–Induced Bends in DNA Heteroduplexes," *Proc. Natl. Acad. Sci. USA*, (1993), vol. 90, pp. 10325–10329.

Kohn, J., et al. "A Cellulose Acetate Immunofixation Technique," *J. Immunol. Methods*, (1978), vol. 20, pp. 325–331.

Ambler, J., et al., "Two New Non–Barbiturate Buffers for Electrophoresis of Serum Proteins on Cellulose Acetate Membranes," *Clin. Chem.* (1980), vol. 26, No. 8, pp. 1221–1223.

Liu, Q., et al., "The SSCP Phenomenon: Addition of HEPES Buffer Dramatically Affects Electrophoretic Mobility," *BioTechniques*, (1998), vol. 25, pp. 50–56.

Kukita, Y., et al., "SSCP Analysis of Long DNA Fragments in Low pH Gel," *Hum. Mutat.*, (1997), vol. 10, pp. 400–407.

Sasaki, T., et al., "ATM Mutations in Patients with Ataxia Telangiectasia Screened by a Hierarchical Strategy," *Hum. Mutat.*, (1998), vol. 12, pp. 186–195.

Orban, L., et al., "Quantitative Gel Electrophoresis of Polystyrene Particles with 20–60nm Radii on 30% Crosslinked Polyacrylamide Gel," *Electrophoresis*, (1987), vol. 8, pp. 465–471.

Chramback, A., et al., "Selected Buffer Systems for Moving Boundary Electrophoresis on Gels at Various pH Values, Presented in a Simplified Manner," *Electrophoresis*, (1983), vol. 4, pp. 190–204.

\* cited by examiner

*Primary Examiner*—Richard D. Lovering
(74) *Attorney, Agent, or Firm*—Rothwell, Figg, Ernst & Manbeck

(57) ABSTRACT pK-matched buffers, each containing two effective buffering components: one weak base and one weak acid which have similar $pK_a$ at 25° C. (within 0.3 pK units On agarose gels, the buffers in various concentrations were tested for separation of double-stranded DNA fragments with various DNA markers, agarose gel concentrations, and field strengths. Mobility was inversely proportional to the logarithm of molecular weight. The buffers provided high resolution without smearing at more dilute concentration than is possible with standard TAE (Tris/Acetate, pH 8.0) or TBE (Tris/Borate, pH 8.3) buffers. The buffers were also tested in 7M urea denaturing LongRanger™ sequencing gels and in non-denaturing polyacrylamide SSCP gels. The pK-matched buffers provide good separation and high resolution, at a broad range of potential pH values. In comparison to TAE and TBE, pK-matched buffers provide higher voltage and current stability, lower working concentration, more concentrated stock solutions, and lower current per unit voltage, resulting in less heat generation.

3 Claims, 13 Drawing Sheets

PK-MATCHED RUNNING BUFFERS FOR GEL ELECTROPHORESIS

CROSS REFERENCE TO RELATED APPLICATION

This application claims the benefit of provisional application Ser. No. 60/127,087, filed Mar. 31, 1999. +gi

GOVERNMENT RIGHTS

This invention was made with partial funding under Grant RO1-HL 39762 from the National Institutes of Health of the United States. The United States government has certain rights in the invention.

BACKGROUND

Since Tiselius pioneered electrophoretic separation of human serum albumin, $\alpha$-, $\beta$- and $\gamma$- globulin in 1937, electrophoresis of biological molecules has been critical to biomedical research (1). Electrophoretic analysis has become more sophisticated, specialized and useful as new types of electrophoresis are developed (2,3). McDonell et al. and Southern offered detailed descriptions of standard agarose gel electrophoresis and its use for DNA analysis (4,5). Pulsed-field agarose gel electrophoresis is an alternative for separation of very large DNA fragments up to 2000 kb (6). Another important application is polyacrylamide gel electrophoresis for separation of small DNA segments, such as dideoxy sequencing analysis (7,8) and SSCP analysis (9–11).

Electrophoresis of nucleic acids in agarose and polyacrylamide gels is generally performed with TAE or TBE buffers. These buffers perform well in many applications, but certain limitations exist. A key limitation is buffering capacity which determines the working concentration and, in turn, determines the rate at which electrophoresis can occur without distortions due to heating. Limiting buffer capacity may require a change of buffer when long electrophoresis times are required, e.g., in mutation scanning using restriction endonuclease fingerprinting or SSCP. TAE buffer cannot be used for sequencing gels because of its low buffering capacity and TAE has a relatively low solubility, such that the maximal stock solution is 20X (2,3). Typically, laboratories that perform sequencing or SSCP-type mutation scanning prepare large volumes of stock solution.

SUMMARY OF THE INVENTION

This invention provides pK-matched buffers comprising a mixture of a weak acid and a weak base which have pKa values at 25° C. within about 0.3 units of one another. The buffers are useful as running buffers for gel electrophoresis of nucleic acids or polypeptides. These pK-matched buffers have the following advantages relative to standard TBE and TAE electrophoresis buffers: 1) high resolution, 2) high electrophoretic stability, 3) low working concentration, and 4) a wide range of pH values for selection.

The invention includes an improved gel electrophoresis method of separating nucleic acids or polypeptides. The improvement comprises running the electrophoresis in a pK-matched buffer of the invention.

DETAILED DESCRIPTION OF THE INVENTION

Figure 1A:
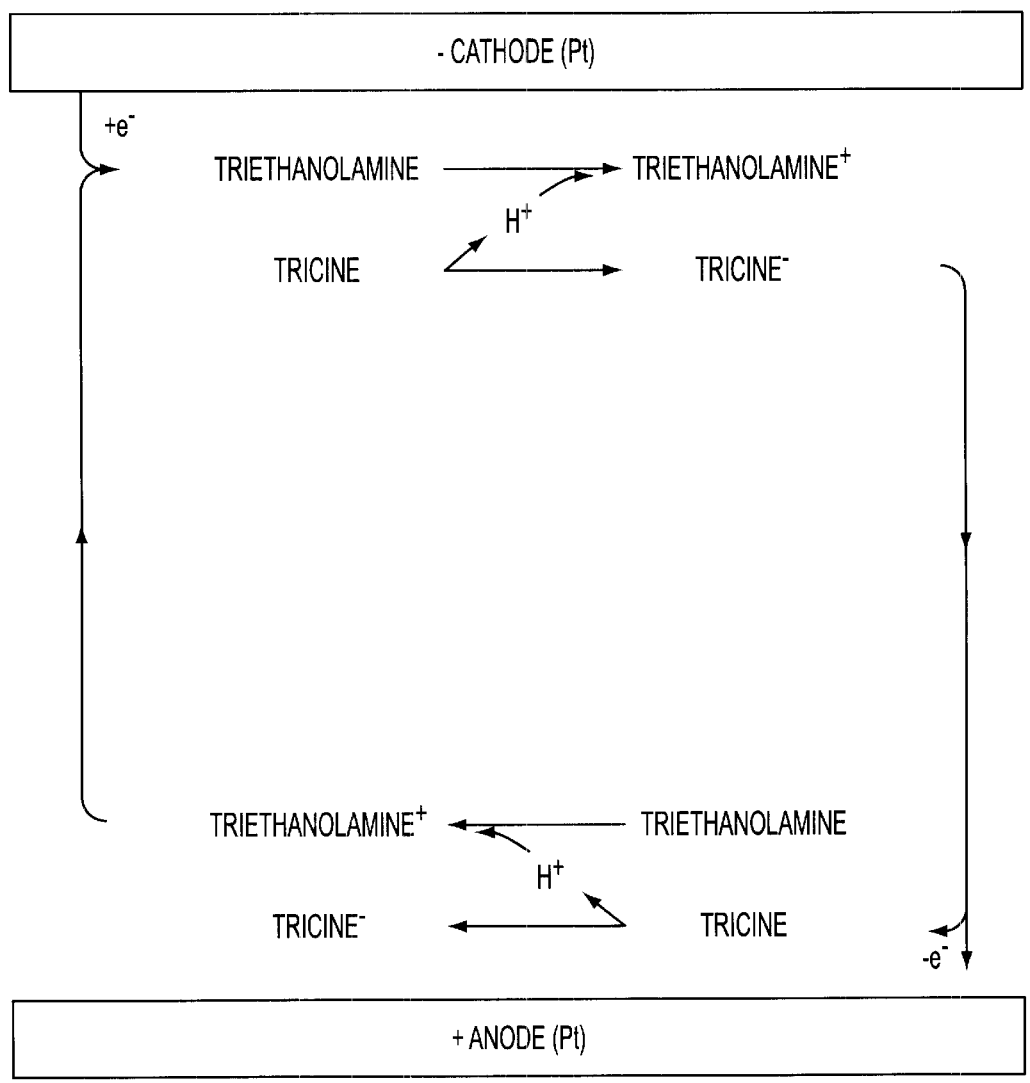
FIG. 1A is a diagram illustrating the principle of pK-matched buffers, using TRI/TRI buffer as an example.

FIG. 1A illustrates the principle of pK-matched buffers, using TRI/TRI buffer as an example. TRI/TRI is a mixture of Triethanolamine and TRICINE. TRICINE is (N-tris [hydroxymethyl]methylglycine. The ions flow between anode and cathode under an electric field strength at a rate which depends on the net charge and the size of the ion. The dissociated, negatively charged TRICINE flows from cathode to anode, gives out an electron, and changes into its neutral form. The dissociated, positively charged Triethanolamine+ flows from anode to cathode, accepts an electron, and changes into its neutral from. The chemical flows happen for balance. Ideally, the flow rates of the two ions are equal and the reservoirs have the same volume. For example, at the anode, due to increase the undissociated TRICINE concentration and decrease in dissociated Triethanolamine+ concentration, chemical balances occur among [TRICINE−], [TRICINE], [Triethanolamine+] and [Triethanolamine], resulting in stable pH and high buffering capacity. The pH may be calculated from an equation: $pH = \frac{1}{2} \times (pK_a + pK_a') + \frac{1}{2} \times 1$ g $\{([TRICINE-] \times [Triethanolamine])/([TRICINE] \times [Triethanolamine+])\}$. It is modifed from Henderson-Hasselbalch equation: $pH = pK_a + 1$ g $([TRICINE-]/[TRICINE])$, or $pH = pK' + 1$ g $([Triethanolamine]/[Triethanolamine+])$.

A series of novel pK-matched buffers were developed and extensively tested as electrophoresis running buffers on agarose gel, denaturing sequencing gel and non-denaturing polyacrylamide gel. These experiments are described below.

MATERIALS AND METHODS

Reagents

Agarose LE and Seakem$^R$GTG$^R$ agarose were purchased from Boehringer Mannheim and Intermountain scientific. LongRanger™ gel was from J. T. Baker. Urea and Tris (Tris[hydroxymethyl]aminomethane; $C_4H_{11}NO_3$; $pK_a=8.3$ at 25° C.; useful pH range 7.0–9.0; FW 121.1) were from Boehringer Mannheim, and Borate ($H_3BO_3$; $pK_a=9.24$ at 25° C.; $pK_{a1}=9.14$, $pK_{a2}=12.74$, $pK_{a3}=13.80$ at 20° C.; FW 61.83) and acetic acid, glacial ($C_2H_3O_2$; $pK_a=4.74$ at 25° C.; FW 60.05) from J. T. Baker. The other buffer components were from Sigma. Triethanolamine (2,2',2"-Nitrilotriethanol; $C_6H_{15}NO_3$; $pK_a=7.8$ at 25° C.; useful pH range 7.3–8.3; FW 149.2), TRICINE (N-tris [Hydroxymethyl]methylglycine; N-[2-Hydroxy-1,1-bis (hydroxymethyl)ethyl]glycine; $C_6H_{13}NO_5$; $pK_a=8.1$ at 25° C.; useful pH range 7.4–8.8; $\Delta pK_a/\Delta T=-0.021$; FW 179.2), Ethanolamine (2-Aminoethanol; $C_2H_7NO$; $pK_a=9.5$ at 25°

C.; useful pH range 8.8–10.2; FW 61.08), CAPSO (3-[Cyclohexylamino]-2-hydroxy-1-propanesulfonic acid; $C_9H_{19}NO_4S$; $pK_a$=9.6 at 25° C.; useful pH range 8.9–10.3; FW 237.3), BIS-TRIS (bis[2-hydroxyethyl]iminotris-[hydroxymethyl]methane; 2-bis[2-Hydroxyethyl]amino-2-[Hydroxymethyl]-1,3-propanediol; $C_8H_{19}NO_5$; $pK_a$=6.5 at 25° C.; useful pH range 5.8–7.2; $\Delta pK_a/\Delta T$=−0.020; FW 209.2); ACES (2-[2-Amino-2-oxoethyl)amino] ethanesulfonic acid; N-[2-Acetamido]-2-aminoethanesulfonic acid; $C_4H_{10}N_2O_4S$; $pK_a$=6.8 at 25° C.; useful pH range 6.1–7.5; $\Delta pK_a/\Delta T$=−0.021; FW 182.2).

Agarose gel electrophoresis

λphage DNA/HindIII and φX174 RF DNA/HaeIII were provided by the Cloning Laboratory of City of Hope. 100 bp DNA Ladder, 1 kb DNA Ladder and High Molecular Weight DNA Marker were purchased from Life Technologies. A phage DNA/HindIII contains eight fragments of 125, 564, 2027, 2322, 4631, 6557, 9416 and 23130 bp; φX174 RF DNA/HaeIII contains 11 fragments of 72, 118, 194, 234, 271, 281, 310, 603, 872, 1078 and 1353 bp; 100 bp DNA Ladder contains 16 fragments of 100, 200, 300, 400, 500, 600, 700, 800, 900, 1000, 1100, 1200, 1300, 1400, 1500 and 2072 bp; 1 kb DNA Ladder contains 23 fragments of 75, 134, 154, 201, 220, 298, 344, 396, 506, 517, 1018, 1636, 2036, 3054, 4072, 5090, 6108, 7126, 8144, 9162, 10180, 11198, 12216 bp; High molecular DNA marker contains 13 fragments of 8271, 8612, 10086, 12220, 15004, 17057, 19399, 22621, 24776, 29942, 33498, 38416, 48502 bp.

Wide mini-sub® cell GT from Bio-Rad (15 cm×16 cm) was used for agarose gel electrophoresis. A horizontal slab gel (10 cm×15 cm×6.6 mm) was cast with a 20-teeth comb (each 0.75 mm×4.8 mm with 15 µl of volume capacity). Triethanolamine/TRICINE (TRI/TRI), Ethanolamine/CAPSO (ETH/CAP), and BIS-TRIS/ACES (BIS/ACE), TAE (Tris/Acetate) and TBE (Tris/Borate) buffers were tested with 600 ml volume. Voltage, current and power were recorded with an EC-400 power supply (E-C Apparatus). 15 µl of sample was loaded and the gel was stained with ethidium bromide for UV photography by a CCD camera (Bio-Rad Gel Doc 1000) and Multi-Analyst® software (version 1.1). Regression equation and correlation coefficient were obtained between the relative mobility to the 2036 bp fragment of 1 kb DNA ladder and the log (base pair). DNA fragments ranging from 1018 bp to 23130 bp in λ DNA marker/HindIII and 1 kb DNA ladder were calculated on 0.6% agarose gel. The mobility was relative to the 600 bp fragment of 100 bp DNA ladder and DNA fragments ranged from 72 bp to 2072 bp in φX174 DNA marker/HaeIII, 100 bp DNA ladder and 1 kb DNA ladder on 2.5% agarose gels. The mobility was relative to the 1636 bp fragment of 1 kb DNA ladder and DNA fragments ranged from 300 bp to 12216 bp in 100 bp DNA ladder and 1 kb DNA ladder were calculated on 1% agarose gels.

Sequence analysis

Exons E and H of the human factor IX gene were amplified with primers I4(17305)-17D and I5(18163)-17U to generate on 858 bp region including exon E, or with primers I7(30412)-17D and E8(31573)-17U for a 1161 bp region of exon H. [Nomenclature as described (13, 14), as an example, E8 (17305)-17D is an oligonucleotide in which the 5' end begins at basepair 17305. The length is 17 bases, and the orientation is "downstream" (D), i.e., in the direction of transcription.] The PCR mixture contained a volume of 25 µl; 50 mM KCl, 10 mM Tris/HCl pH 8.3, 1.5 mM $MgCl_2$ for exon E or 2.5 mM $MgCl_2$ for exon H, 200 µM of each dNTP, 0.1 µM of each primer, 0.5 U of Taq DNA polymerase (Boehringer Mannheim) and 250 ng of genomic DNA. Denaturation was at 94° C. for one minute, annealing was at 55° C. for one minute, and elongation was at 72° C. for three minutes, for a total of 30 cycles. The PCR product was purified by Microcon® 100 (Amicon). Sequencing reaction was performed with Thermo Sequenase radiolabeled terminator cycle sequencing kit (Amersham Life Science) utilizing primer I5(17866)-19U for exon E or primer E8(31164)-16U for exon H. Bio-Rad-Sequi-Gen GT sequencing cell (38 cm×50 cm×0.4 mm) was used. A 7M urea 6% LongRanger™ gel with 73 shark-tooth lanes was electrophoresed with a total of 3000 ml buffer at 80 W constant power and 2200–2500 volts (Bio-Rad PowerPac 3000 Power Supply). TRI/TRI, ETH/CAP, and BIS/ACE buffers at 30 mM, and TBE buffer at 50 mM were tested. After a preliminary electrophoresis for 30 minutes, three µl of each sample was loaded and electrophoresed for two hours at 45° C. The gel was dried and exposed to Kodak BioMax MR film for autoradiography. The sequence was read by SEQ-EASY™ digitizer-talker and DNA*™ software (DNASTAR) and was aligned with wildtype sequence.

Dideoxy fingerprinting (ddF)

Samples were amplified as mentioned above, except with primers I1(6094)-30D and 13(6878)-27U for a 785 bp region of exons B/C or with primers I7(30646)-34D and E8(31645)-31U for a one kb region of exon H in the human factor IX gene. The ddF reactions were identical to a single dideoxy component of the sequencing reactions, with the exception of primers and loading buffer: primer I1(6272)-22D for exons B/C or with [α-$^{33}$P]ddGTP and primer I7(30851)-19D for exon H and 15 µl of stop/loading buffet (50% formamide, 7M urea, 2 mM EDTA, 0.05% bromophenol and 0.05% xylene cyanol) was added to each tube.

A non-denaturing gel (45 cm×37.5 cm×0.4 mm) was electrophoresed by using a water-cooled PokerFace™ SE 1500 sequencing apparatus with total 4000 ml buffer at 12–15 watts constant power for 6–16 hours. TRI/TRI and ETH/CAP buffers at 30 mM, and TBE buffer at 50 mM were tested. On the ddF gel, an informative dideoxy component was easily detected by a missing or an extra segment. The shifted mutation-containing segments in the SSCP component were scored by comparison with wildtype control. Typically, a migration change of ½ band width on the upper part of the gel or ¼ band width on the lower part was the limit of resolution (15).

RESULTS

Properties of the buffers

Figure 1B:
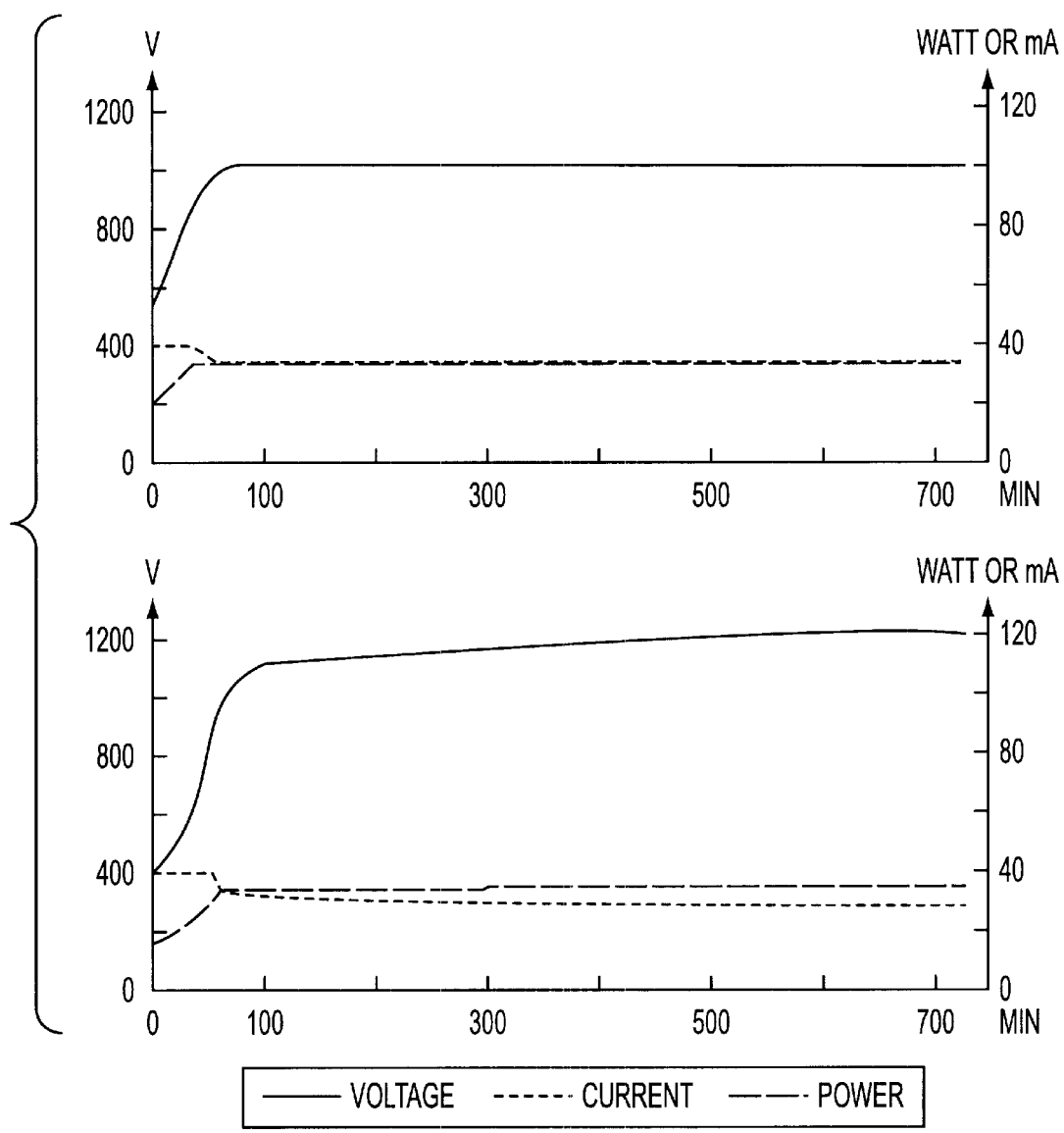
FIG. 1B is a comparison of electrophorectic stability between pK-matched buffer ETH/CAP and standard TBE buffer.
Figure 2A:
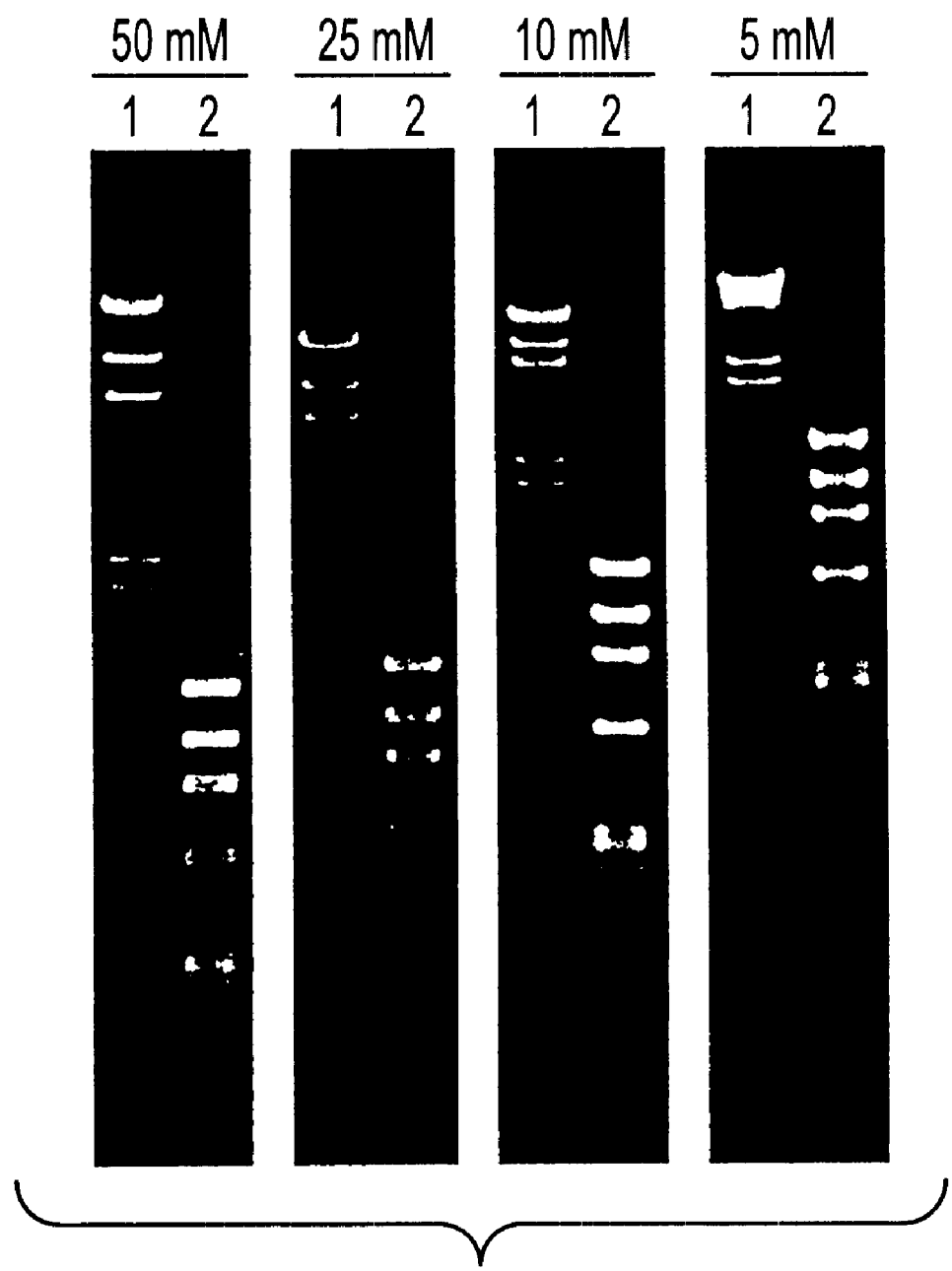
FIGS. 2A, 2B and 2C are photographs showing the effects of concentration of three pK-matched buffers, TRI/TRI, ETH/CAP, and BIS/ACE.
Figure 2B:
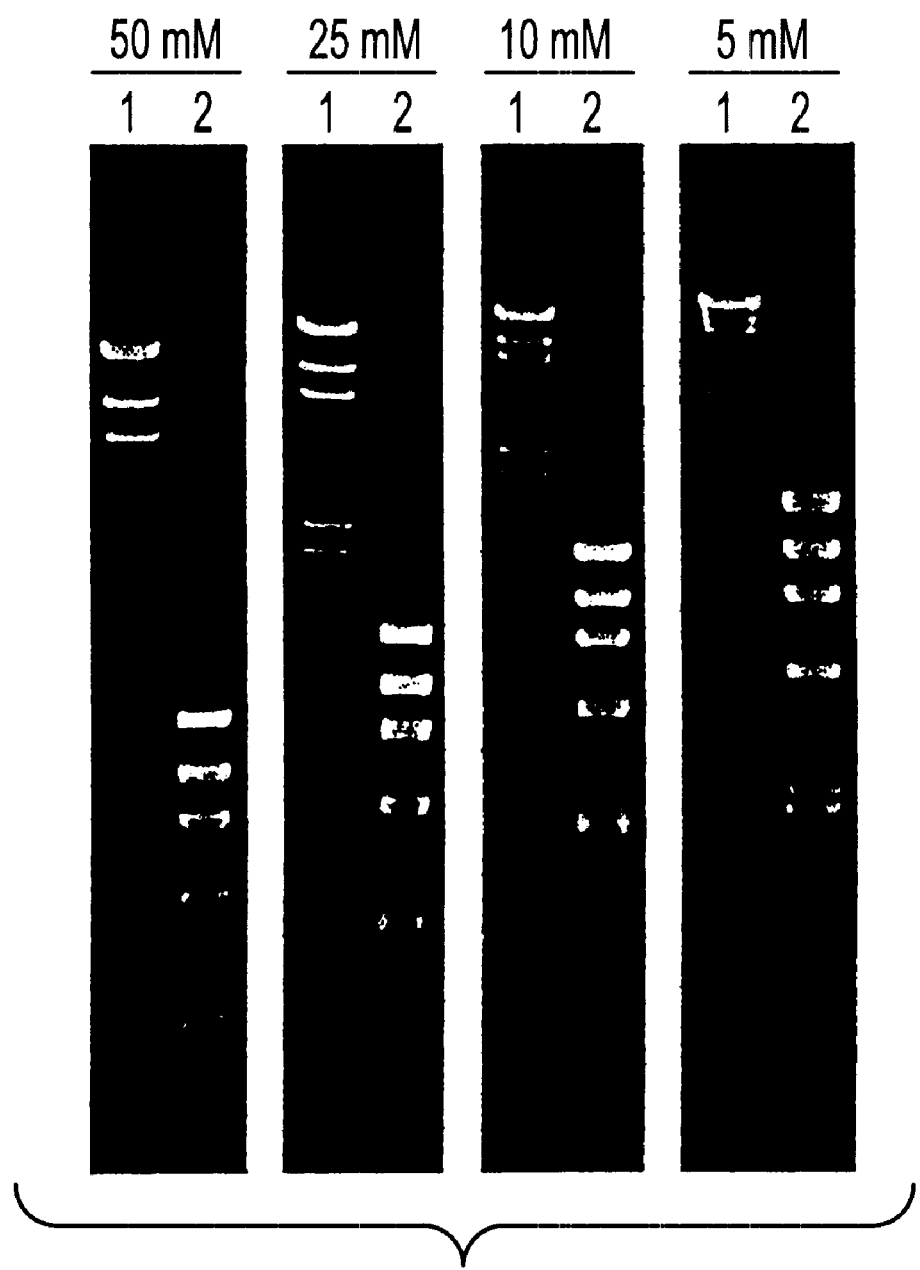
Figure 2C:
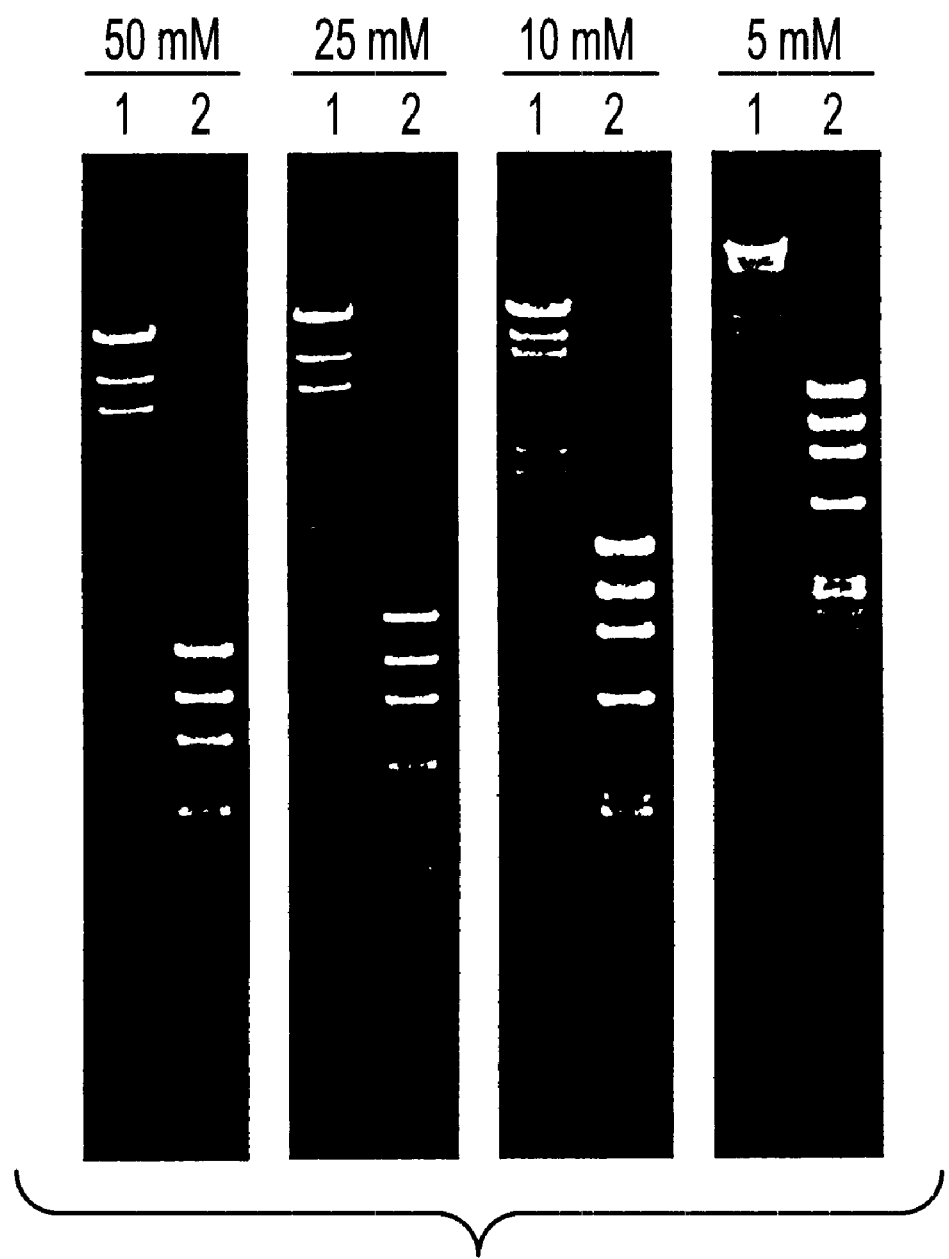
Figure 2D:
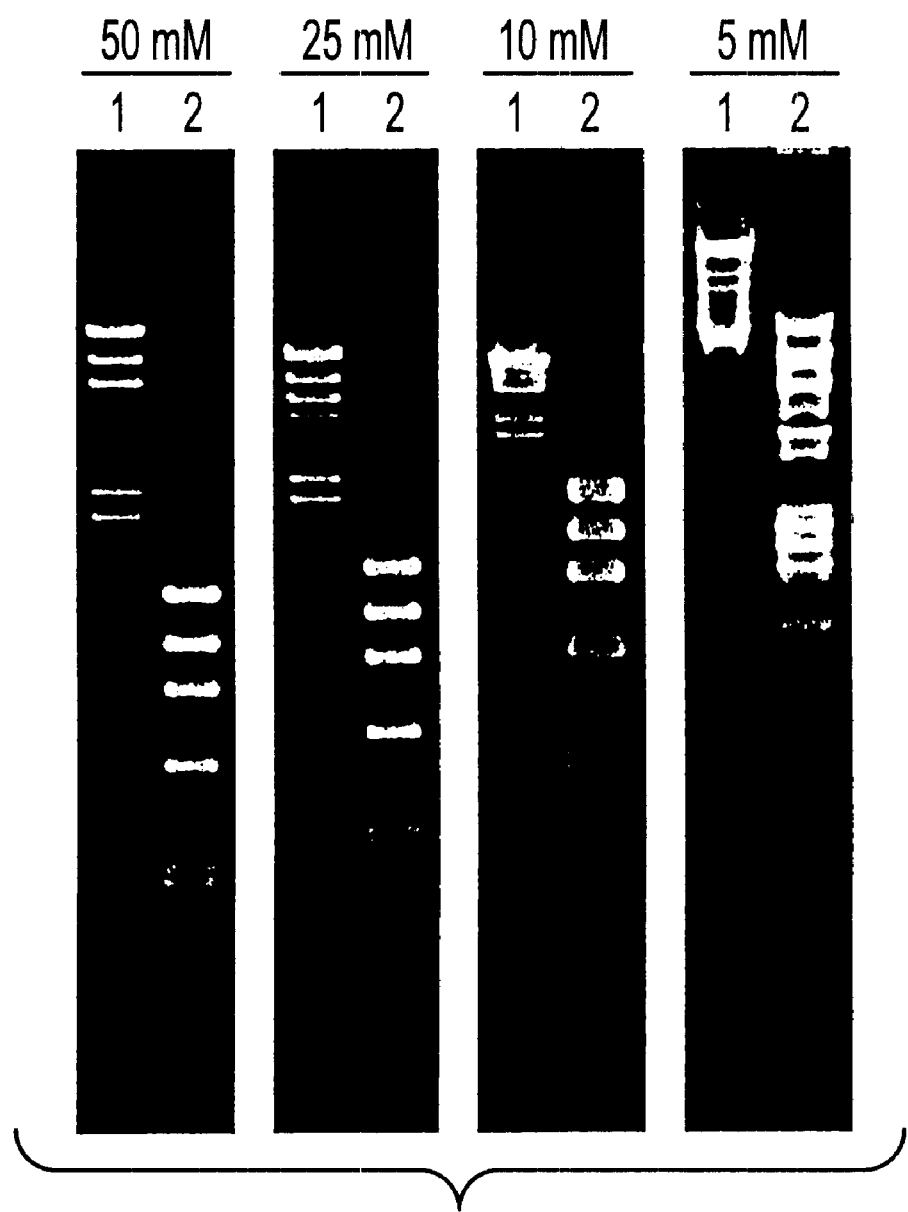
FIGS. 2D and 2E are photographs showing the effects of concentration of standard TBE and TAE buffers.
Figure 2E:
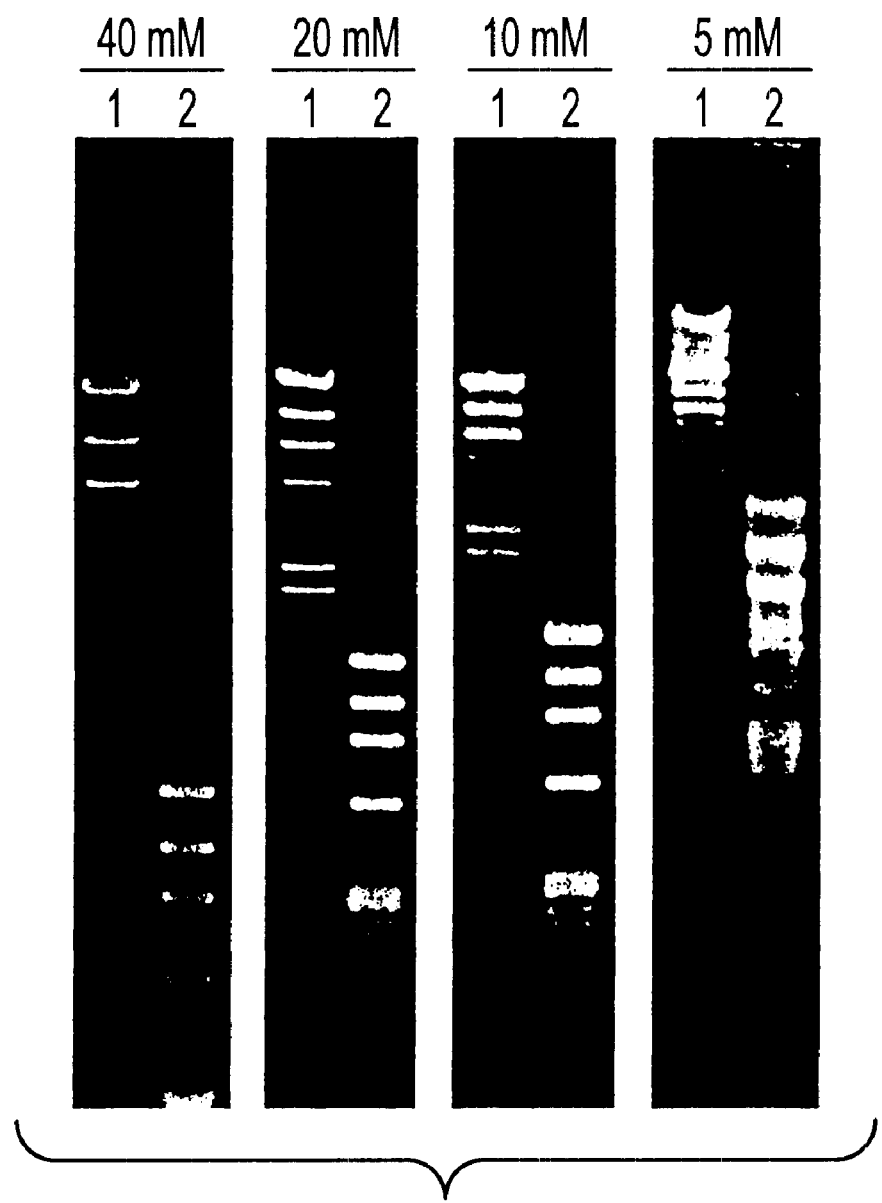

As illustrated in FIG. 1A, pK-matched buffers are predicted to provide more stable current and voltage during electrophoresis because both cations and anions can be regenerated at the anode and the cathode, respectively Referring to FIG. 1B, these predictions were confirmed when the electrophoretic stability of pK-matched buffers was compared with that of TBE by performing an SSCP-type analysis for 12 hours with the ALF-express fluorescent sequencer. 8% non-denaturing polyacrylamide-type gel (29.5 cm×30 cm×0.5 mm) was electrophoresed for 12 hours with the ALFexpress™ DNA Sequencer (Pharmacia Biotech) with 1000 ml of electrophoresis buffer in each of upper and lower reservoirs. The voltage, current and power were set at 1500 V, 40 mA and 35 watt and the gel was electrophoresed for 12 hours at 35° C. The ETH/CAP pK-matched buffer at 30 mM (Upper) was compared with TBE buffer at 50 mM (Lower). The Y axes represent the observed voltage (-), current ( - - - ) and power ( - - ). The X axis is the running time. pK-matched buffer at 30 mM was shown more stable with the voltage, current and power than the TBE buffer at 50 mM. The same results were obtained when pK-matched buffer was used at 50 mM and when denaturing sequencing gels were applied.

Table 1 shows the chemical properties of three pK-matched buffers of Triethanolamine/TRICINE (TRI/TRI), Ethanolamine/CAPSO (ETH/CAP), and BIS-TRIS/ACES (BIS/ACE). The two components of each buffer are a weak acid and a weak base having similar $pK_a$ values ($|\Delta pK_a|\leq 0.3$) The pH of each buffer is close to the average of $pK_a$ values with 1:1 molar mixture of acid and base ($|pH-\frac{1}{2}\times(pK_a+pK_a')|\leq 0.1$) The pH of the buffers range from 6.7 to 9.6. The buffers had been stored for 4–12 months and were chemically stable (CAPSO is light sensitive and should be stored in dark). For example, 30 mM TRI/TRI buffer contains 30 mM Triethanolamine and 30 mM TRICINE (pH 7.9 at 25° C.). Table 2 summarizes the physical properties of current, power, and voltage in agarose gel electrophoresis. pK-matched buffer was compared with TBE and TAE at various concentrations from 50 mM to 5 mM (1X TAE: 40 mM Tris/26.6 mM Acetate, 1 mM EDTA, pH 8.0).

Agarose gel electrophoresis

Linear duplex DNA molecules migrate at a rate that is inversely proportional to the logarithm of their molecular weight (16). DNA markers, which sizes ranged from 48.5 kb to 72 bp, were electrophoresed on 1% agarose gels at various buffer concentrations with constant voltage (6 voltage/cm for 1.5 hour. The mobilities of the pK-matched buffers were compared with TBE and TAE buffers from 50 mM to 5 mM. The results are shown in FIG. 2: A. TRI/TRI, B. ETH/CAP, C. BIS/ACE, D. TBE; Lanes 1–4, 5–8, 9–12 and 13–16 were at 50, 25, 10 and 5 mM. E. TAE, at 40, 20, 10 and 5 mM, respectively. DNA markers: In lanes 1, 5, 9 and 13 were 500 ng of λ DNA/HinHIII; in lanes 2, 6, 10 and 14 were 500 ng of φX174 DNA/HaeIII; in lanes 3, 7, 11 and 15 were 1000 ng of 100 bp DNA ladder; in lanes, 4, 8, 12 and 16 were 1000 ng of 1 kb DNA ladder. The top of the image was the well position.

The relative mobilities of the DNA fragments from 100–12000 bp were inversely proportional to the log of the sizes and the correlation coefficients (r) were close to −1 under each condition (Table 2). With decreased buffer concentrations from 50 mM to 5 mM, absolute mobilities of the DNA fragments decreased, typically by a factor of 1.3–2.0 (FIG. 2).

The broadening of bands were also analyzed. Broad bands result from diffusion of small DNA molecules through the gel (2,12) and from dispersion of large DNA molecules through entanglement (17). The segments of small sizes became sharper with diluted buffer concentration, but the band of the 2072 bp fragment in the 100 bp DNA ladder broadened. When the concentration was as low as 5 mM, pK-matched buffer still provided high resolution without smearing, while TBE or TAE buffers did not (FIG. 2).

Figure 3A:
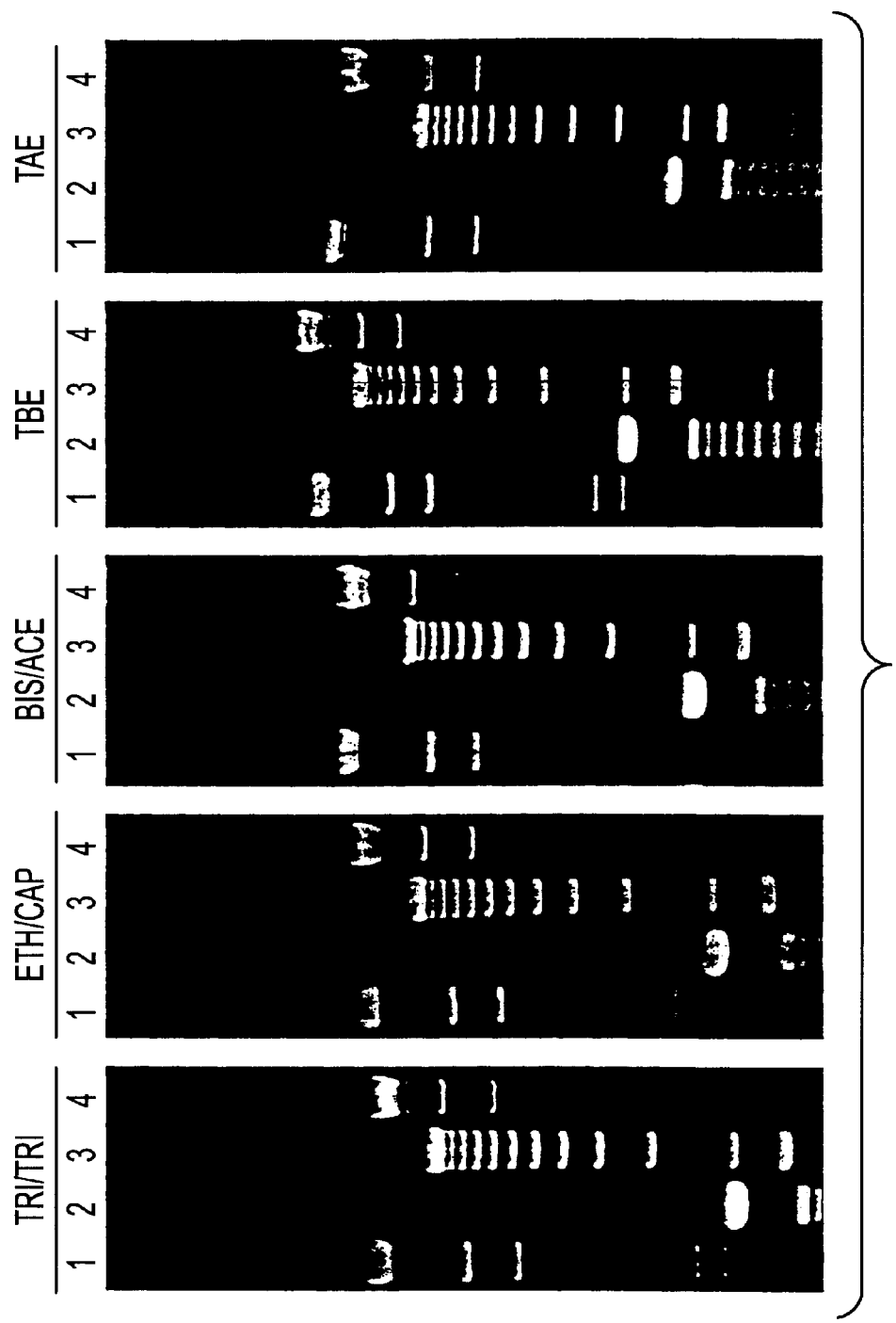
FIGS. 3A–3C are photographs showing the effects of agarose concentration and applied voltage using pK-matched buffers TRI/TRI, ETH/CAP, and BIS/ACE and standard buffers TBE and TAE.

The pK-matched buffers were tested at 15 mM and compared with 1X TBE and 1X TAE buffers to determine the effects of agarose concentration and applied voltage. The results are shown in FIG. 3:

FIG. 3A: 0.6% agarose gel was electrophoresed at 4 volts/cm for 3 hours. DNA markers: In lane 1 was 500 ng of λ DNA/HinHIII; in lane 2 was 1 µg if 100 bp DNA ladder, in lane 3 was 1 µg of 1 kb DNA ladder. The 100 bp DNA ladder was electrophoresed out of the gel.

Figure 3B:
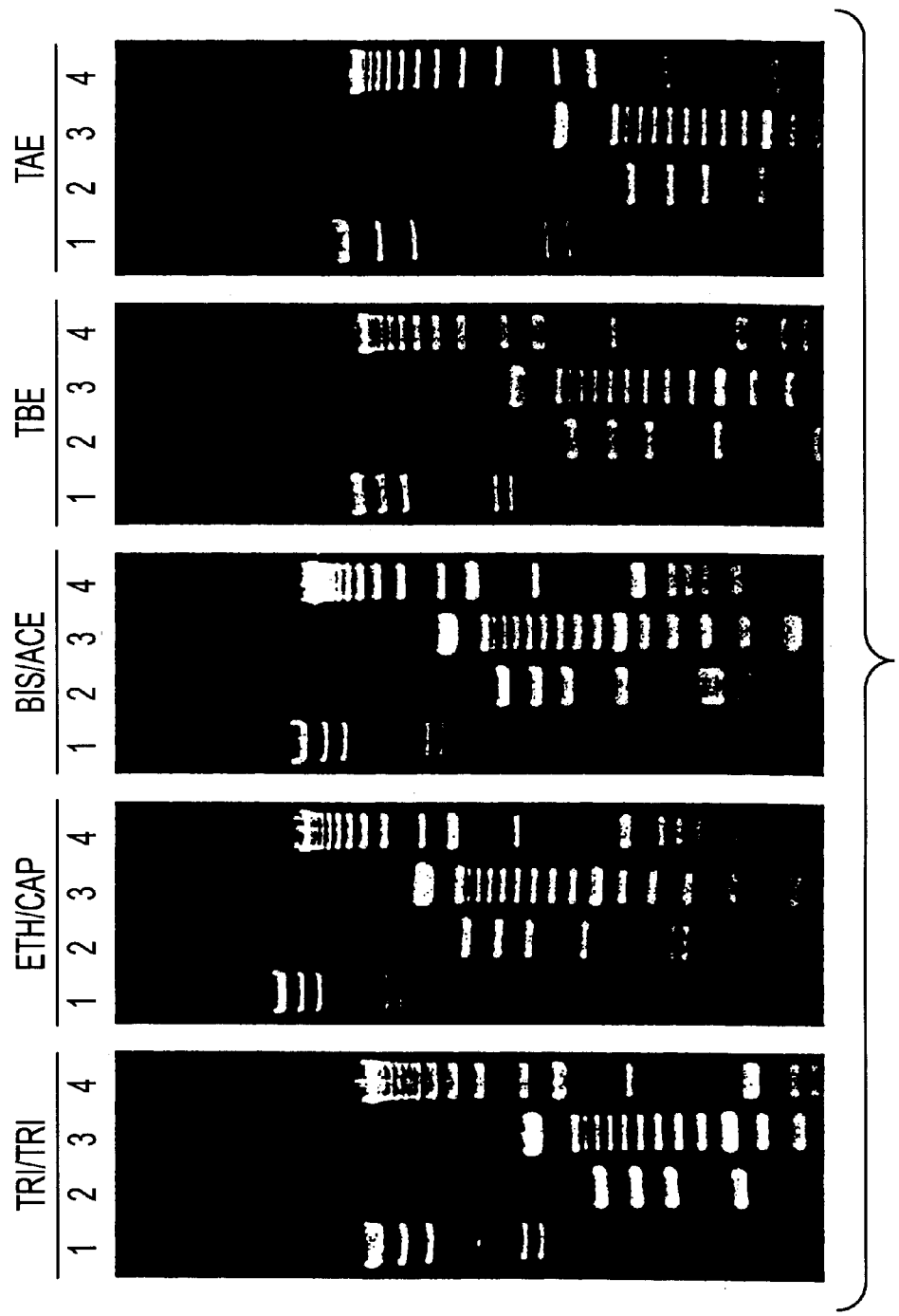

FIG. 3B: 2.5% agarose gel was electrophoresed at 6 volts/cm for 90 minutes. DNA markers: in lane 1 was 1 µg of 100 bp DNA ladder; in lane 2 was 1 µg of 1 kb DNA ladder.

Figure 3C:
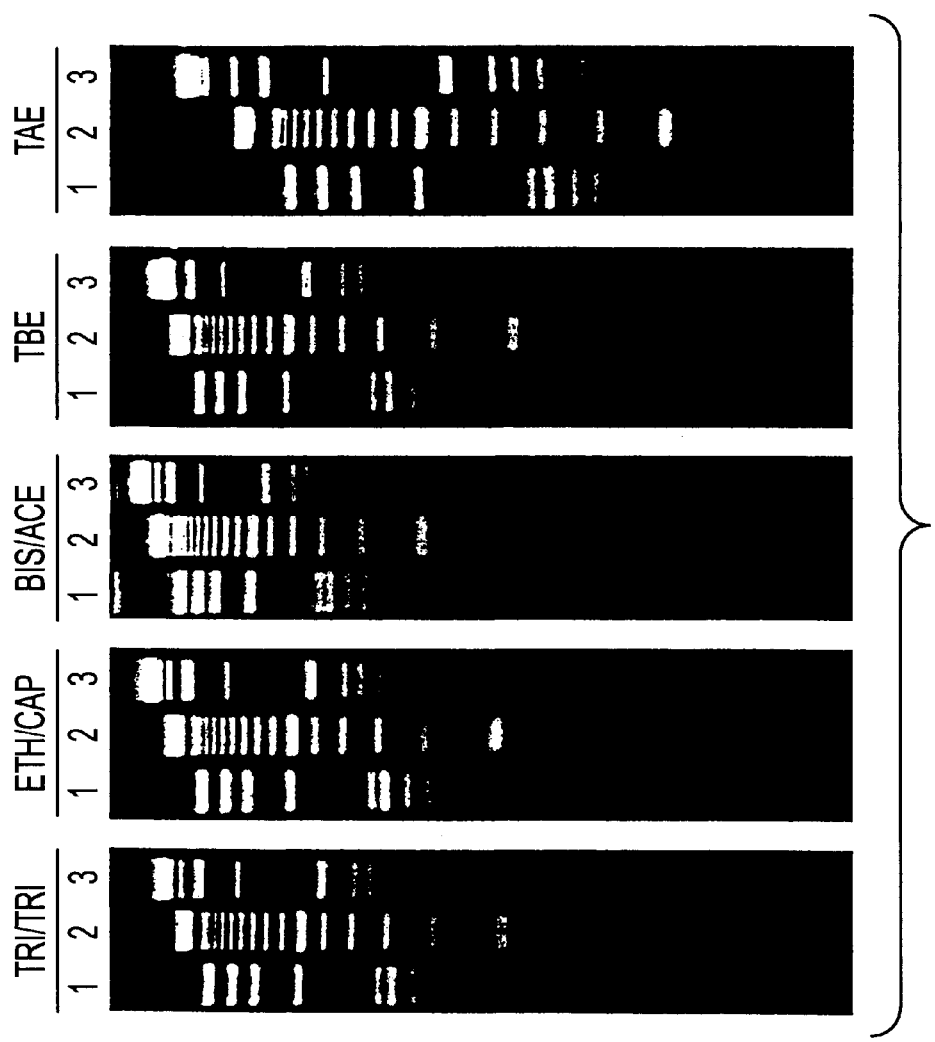

FIG. 3C: 1% agarose gel was electrophoresed at 12 volts/cm for 45 min. DNA markers were the same as in B.

The quality of separation achieved with the pK-matched buffers at 15 mM was as high as or better than that achieved with 1X standard concentrations of TBE (50 mM) or TAE (40 mM), when the effects of low agarose gel concentrations and high voltage were examined (FIG. 3 and Table 3).

Sequence analysis

Figures 4A, 4B, 4C, 4D:
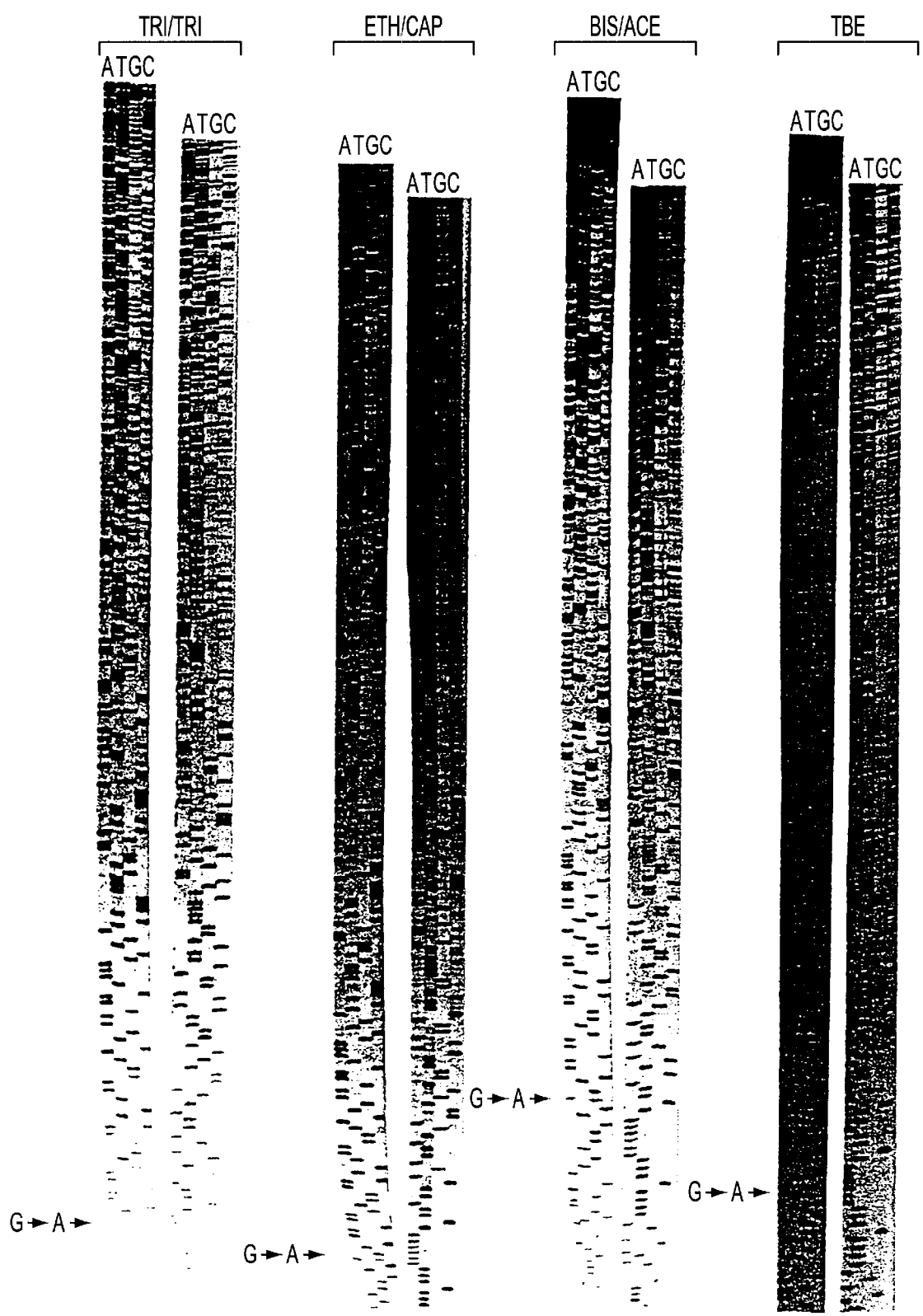
FIGS. 4A–4D are autoradiographs showing the effects of the pK matched buffers TRI/TRI, ETH/CAP, and BIS/ACE and standard buffer TBE in Sanger dideoxy sequencing analysis.

Sanger dideoxy sequencing analyses were performed on 7M urea LongRanger™ gels for exons H and E in the factor IX gene (7,8). TRI/TRI, ETH/CAP and BIS/ACE buffers at 30 mM were compared with 1X TBE buffer. The results are shown in FIG. 4: A. TRI/TRI buffer, B. ETH/CAP buffer, C. BIS/ACE buffer. The three pK-matched buffers were used at 30 mM. D. 1X TBE buffer (50 mM) for comparison. Two regions of exons H (left) and E (right) in the factor IX gene were shown. Under each condition, the termination segments were separated with high resolution. The sequences were obtained accurately up to 360 bases for exon H and up to 230 bases for exon E, which were read to the last base by SEQ-EASY™ digitizer-talker and DNA*™ software. A heterozygous mutation C-T in exon H was detected with all conditions (FIG. 4). Similar results were observed when other regions were sequenced (data not shown).

Dideoxy fingerprinting

Dideoxy fingerprinting (ddF) was used to efficiently explore the SSCP sensitivity of different conditions. ddF is a hybrid technique between SSCP and Sanger dideoxy sequencing (9,10,15). ddF reaction is performed with one primer and one dideoxy terminator; then the terminated single-stranded segments are electrophoresed through one lane of a non-denaturiny gel. The ladder of segments subsequent to a mutation constitutes the SSCP component, which contain the same mutation but differ at the 3' ends.

Nondenaturing conformation-sensitive electrophoresis of markedly different sized segments such as that performed with dideoxy fingerprinting, pose a challenge for electrophoresis buffers. Sometimes TBE buffer must be changed during electrophoresis in order to maintain resolution.

Figure 5A:
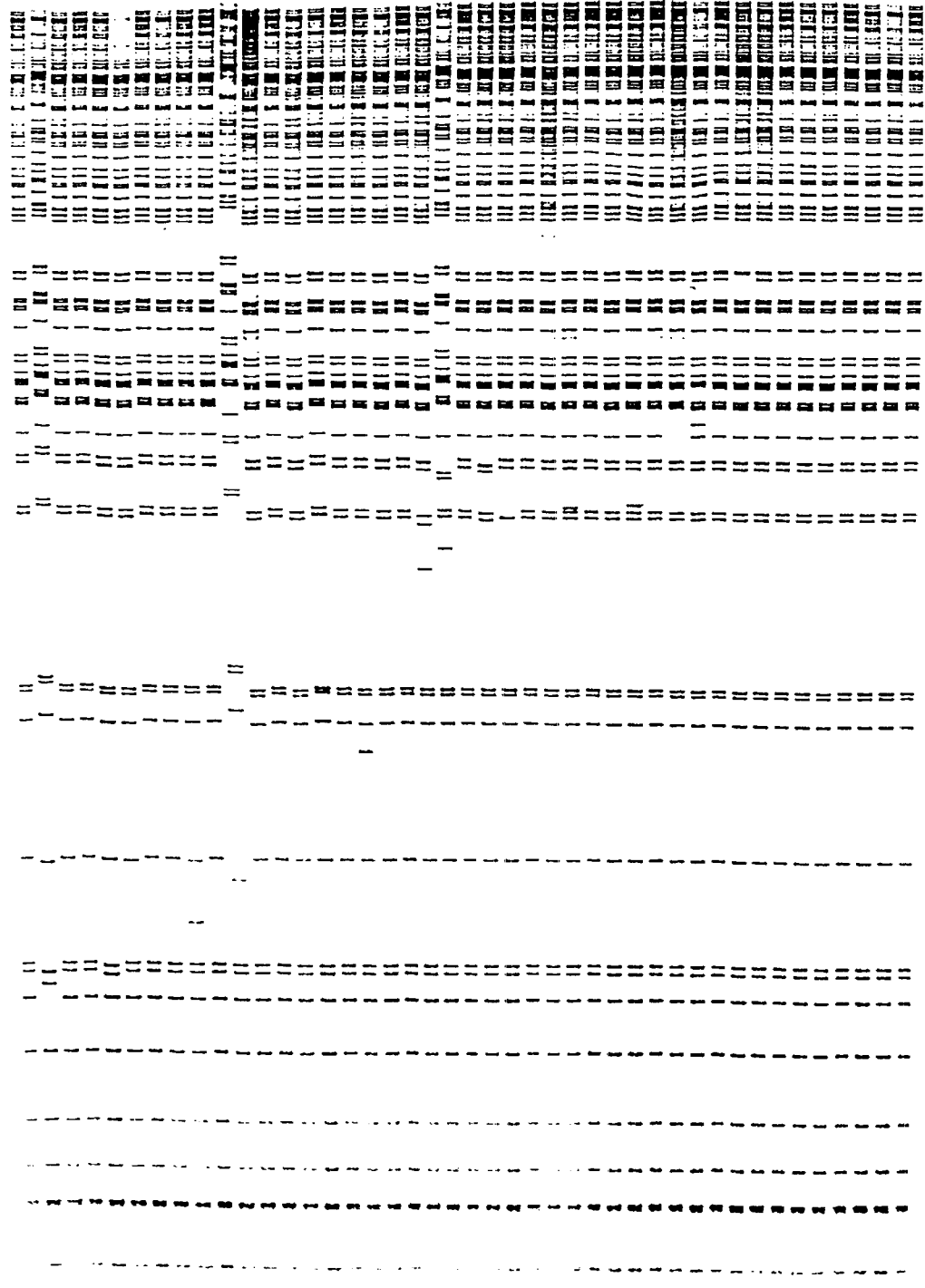
FIGS. 5A and 5B are autoradiographs showing the effects of pK-matched buffer TRI/TRI and standard buffer TBE in dideoxy fingerprinting (ddF).
Figure 5B:
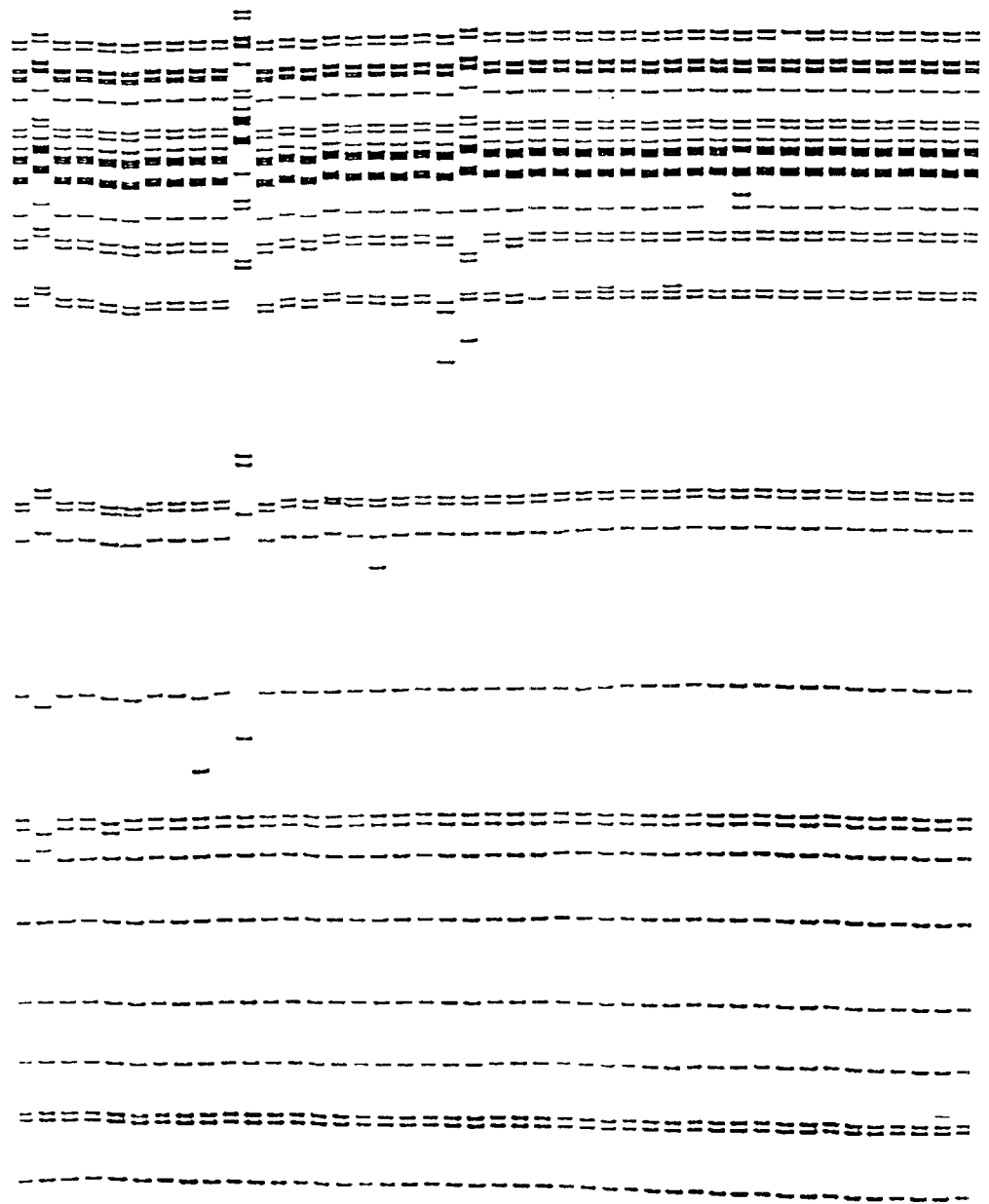

TRI/TRI and ETH/CAP buffer were compared with TBE buffer. The results for TRI/TRI and TBE are shown in FIGS. 5A and 5B, respectively. ddF gels were performed with (A) splice 30 mM TRI/TRI and (B) 1X TBE for exons B/C. The segments up to 300 bases were scored for the first 22 mutations, in which the number of the mutation-containing segments varied from 15 to 26, depending on the location of the mutation. The average efficiencies of SSCP component were 71% for both the conditions, but variable efficiencies of an individual mutation varied. The efficiencies between the two conditions for each mutation were correlated (coefficient=0.88).

10% PAGE$^{plus}$ gels were electrophoresed at 20° C. Lanes 1–28 were hemizygous for the following mutations in exons B/C. 1:C6364T; 2:G6365T; 3:G6365A; 4:G6374A; 5:G6375T; 6:G6376C; 7:A6379G; 8:G6385A; 9:G6394A; 10:A6398G; 11:T6401C; 12:G6436A; 13:T6442C; 14:G6451C; 15:G6454A; 16:C6460T; 17:G6461A; 18:G6461C; 19:G6463A; 20:G6463C; 21:C6488T; 22:T6495C; 23:C6575G; 24:A6653G; 25:G6677C; 26:A6690T; 27:T6696G; 28:A6693G. Lane C was wildtype control.

Other electrophoresis conditions were also tested, which included gel matrices of MDE (FMC BoiProducts), HR1000 (Genomyx), PAGE$^{plus}$ (Amresco), and Dcode™ (Bio-Rad); additives of glycerol, urea, Resolver Gold™ and PEG; and temperatures at 20° C. and 8° C. Twenty-two electrophoretic conditions were tested with different combinations of the buffers, gel matrices, additives, and temperatures. The pK-matched buffers gave sharp bands with resolution at least equivalent to that of TBE (FIG. 5B).

Other pK-matched buffers

Two other pK-matched buffers of 2-Amino-2-methyl-1-propanol ($pK_a$ 9.7)/CAPSO ($pK_a$ 9.6) with pH 9.6 at 25° C., and Triethanolamine ($PK_a$ 7.8)/HEPES (N-[2-Hydroxyethyl)]piperazine-N'-[2-ethanesulfonic acid, $pK_a$ 7.5) with pH 7.6+ at 25° C. were also tested and similar results were observed (data not shown).

The pK-matched buffers in the present study were chosen such that the $pK_a$ of the acid and the $pK_a'$, of the base were within 0.3 units of one another. In each of the pK-matched buffers, the ionic strength (M) of each component is $\leq 50\%$ of its molar concentration, because $pK_a$ of the acid is $\geq pK_a'$ of the base, which contributes to the electrophoretic stability (Table 1). The ionic strength of each component is calculated from Henderson-Hasselbalch equation to be 12.4 mM to 14.2 mM in 30 mM pK-matched buffers. Each of [Tris$^+$] and [Acetate$^-$] is 26.6 mM in 40 mM TAE buffer (pH 8.0); [Tris$^+$] is 25.0 mM in 50 mM TBE (pH 8.3) with Borate complex formation. TRI-TRI buffer is particularly advantageous for routine analysis in molecular biology laboratories, since 200X stocks can conveniently be produced.

In summary, pK-matching buffers were developed and tested on agarose gels for separation of double-stranded DNA segments, on denaturing polyacrylamide gels for sequencing analysis, and on non-denaturing gels for SSCP analysis. High electrophoretic stability and high resolution were observed even at low working concentrations.

In the experiments, parameters, such as gel concentration, chamber capacity, voltage and power, were set as the optimal for TBE and TAE buffers, so the pK-matched buffers should be even better with their optimal conditions. Because of the higher electrophoretic stability of a pK-matched buffer, the reservoirs of electrophroesis cells may be eliminated, or the volume of the reservoirs may be greatly reduced, to 50% or less of the volume of reservoirs in electrophoresis cells using TAE or TBE buffers, especially for agarose gel electrophoresis. For example, a Bio-Rad cell used for agarose gel electrophoresis has two reservoirs with a total volume of 600 μl. These can be eliminated or reduced to a total volume less than 300 μl for use with pK-matched buffers of this invention.

Our invention is not limited to the particular pK-matched buffers used on our experiments. The invention includes buffers prepared by mixing any weak acid and any weak base having pKa values within about 0.3 units of one another. pK-matched buffers can be generated for any desired pH value, so long as appropriate acids and bases are available. pK-matched buffers are useful for electrophoresis analysis of proteins and small molecules.

A variety of other buffers have been used for electrophoresis: (3,18–20), e.g., Tris/phosphate (1X TPE: 90 mM Tris/28 mM phosphoric acid/2 mM EDTA), Alkaline "running buffer" (1X:50 mM NaOH, 1 mM EDTA, pH 12–13), Tris/glycine (1X:25 mM Tris/250 mM glycine, 0.1% SDS, pH 8.3 for SDS-polyacrylamide gel), Tris/Taurine (1X:89 mM Tris/29 mM Taurine/0.5 mM EDTA, pH 9.0) (21), Barbitone/acetate (pH 8.6, a standard buffer for immuno-electrophoresis and separation of serum protein) (22) and Non-barbitone buffer (23), and some other buffers (24–28). These above buffers either contain only one effective component or two more effective components without pK matching.

TABLE 1

Chemical properties of pK-matched buffers

| Buffer[a] | First Component | | Second Component | | pH[b] | Mole Ratio | Stock Conc. M |
|---|---|---|---|---|---|---|---|
| | Base | $pK_a'$ | Acid | $pK_a$ | | | |
| TRI/TRI | Tri-ethanolamine | 7.8 | TRICINE | 8.1 | 7.9 | 1:1 | 3 |
| ETH/CAP | Ethanol-amine | 9.5 | CAPSO | 9.6 | 9.6 | 1:1 | 0.5 |
| BIS/ACE | BIS-TRIS | 6.5 | ACES | 6.8 | 6.7 | 1:1 | 0.5 |

[a]The three buffers were made with Milli-Q deionized water (Millipore) and filtered through 0.2 μm Nalgene[R] filter. EDTA may be added at 0.5 mM of working concentration.
[b]pH was determined at 30 mM and at 25° C.

TABLE 2

Comparison on agarose gel[a]

| Buffer | Physical Property | | | | Separation | |
|---|---|---|---|---|---|---|
| | Conc. (mM) | Power (Watt) | Current (mA) | Heating | Regression Equation[b] | Correlation Coefficient (x)[b] |
| TRI/TRI | 50 | 6.5 | 70 | + | y = −1.30x + 4.55 | −0.992 |
| | 25 | 3.2 | 40 | No | y = −1.29x + 4.53 | −0.992 |
| | 10 | 1.2 | 16.5 | No | y = −1.34x + 4.42 | −0.980 |
| | 5 | 0.6 | 9.5 | No | y = −1.33x + 4.14 | −0.942 |
| ETH/CAP | 50 | 9.3 | 90 | + | y = −1.24x + 4.48 | −0.993 |
| | 25 | 4.5 | 50 | No | y = −1.16x + 4.43 | −0.992 |
| | 10 | 1.8 | 23 | No | y = −1.27x + 4.38 | −0.979 |
| | 5 | 0.9 | 13 | No | y = −1.32x + 4.13 | −0.939 |
| BIS/ACE | 50 | 7.0 | 80 | No | y = −1.21x + 4.47 | −0.993 |
| | 25 | 3.5 | 43 | No | y = −1.23x + 4.49 | −0.992 |
| | 10 | 1.5 | 19 | No | y = −1.29x + 4.38 | −0.982 |
| | 5 | 0.7 | 9.5 | No | y = −0.97x + 4.08 | −0.971 |
| TBE | 50 | 4.5 | 50 | No | y = −1.09x + 4.38 | −0.988 |
| | 25 | 2.7 | 32 | No | y = −1.32x + 4.443 | −0.978 |
| | 10 | 1.2 | 13 | No | y = −1.03x + 4.37 | −0.967 |
| | 5 | 0.6 | 8 | No | y = −1.14x + 3.99 | −0.914 |
| TAE | 40 | 10.5 | 112 | ++ | y = −1.33x + 4.57 | −0.996 |
| | 20 | 5.5 | 62 | + | y = −1.50x + 4.73 | −0.992 |

TABLE 2-continued

Comparison on agarose gel[a]

| Buffer | Physical Property | | | | Separation | Correlation |
|---|---|---|---|---|---|---|
| | Conc. (mM) | Power (Watt) | Current (mA) | Heating | Regression Equation[b] | Coefficient (x)[b] |
| | 10 | 2.5 | 30 | No | y = −1.33x + 4.61 | −0.988 |
| | 5 | 1.5 | 18 | No | y = −1.33x + 4.61 | −0.988 |

[a]1% agarose gel was run at 6 voltage/cm for 90 minutes to separate DNA markers of λ DNA/HinIII, ΦX174 DNA/HaeIII, 100 bp DNA ladder and 1 kb DNA ladder.
[b]Regression equation were by the least square method obtained between the relative mobility to the 1636 bp fragment of 1 kb DNA ladder and the log (base pair). DNA fragments ranging from 100 bp to 12216 bp in the 100 bp DNA ladder and 1 kb DNA ladder were calculated. The correlation coefficient (r) was obtained with the 99% confidence interval overlaps with zero.

TABLE 3

Test of pK-matched buffers on agarose gel

| Buffer | Conc. (mM) | 0.6% Agarose at 4 volts/cm[a] | | 2.5% Agarose at 6 volts/cm[b] | | 1% agarose at 12 volts/cm[c] | | Heat |
|---|---|---|---|---|---|---|---|---|
| | | Power (Watt) | Current (mA) | Power (Watt) | Current (mA) | Power (Watt) | Current (mA) | |
| TRI/TRI | 30 | 1.8 | 31 | 3.5 | 43 | 19.5→28[e] | 100→140[e] | + |
| | 15 | 0.9 | 16 | 1.8 | 22 | 10→11.5 | 55→65 | No |
| ETH/CAP | 30 | 1.8 | 34 | 5.5 | 63 | 26→35 | 130→180 | + + |
| | 15 | 0.9 | 17 | 2.5 | 34 | 13.5→16 | 70→80 | + |
| BIS/ACE | 30 | 1.8 | 34 | 4 | 50 | 22 | 110 | + |
| | 15 | 0.9 | 17 | 2 | 25 | 10 | 55 | No |
| TBE | 50 | 2.5 | 37 | 4.5 | 50 | 22→30 | 105→150 | + |
| | 30 | 1.3 | 27 | 3.5 | 46 | 7.8→8.0 | 65→70 | No |
| | 15 | 0.7 | 16 | 2 | 24 | 4 | 37 | No |
| TAE[d] | 40 | 4.5 | 78 | 10.5 | 112 | >>35[f] | >>200[f] | + + + |
| | 30 | 3.6 | 65 | 9 | 100 | 17.2→22.5 | 137→168 | + + |
| | 15 | 1.9 | 35 | 4.5 | 50 | 8→8.7 | 68→77 | No |

[a]Electrophoresis for three hours.
[b]Electrophoresis for 90 minutes.
[c]Electrophoresis for 45 minutes.
[d]Some other heating occurred when TAE buffer was used at 40–30 mM at 4–6 volts/cm.
[e]Obvious change in power and current between the beginning and end.
[f]Larger than the maximum recorded point.

RFERENCES

1. Tiselius, A. (1937) *Annu. Rev. Med.,* 48, 231–240.
2. Voytas, D. (1988) in Current Protocols in Molecular Biology (Ausubel, F. M., Brent, R., Kingston, R. E., Moore, D. D., Seidman, J. G., Smith, J. A., and Struhl, K. Eds.), pp. 2.5.1–2.5.9, John Wiley & Sons, Brooklyn, New York.
3. Sambrook, J., Fritsch, E. F., and Maniatis, T. (1989) in Molecular Cloning: A Laboratory Manual. pp. 6.1–6.62, Cold Spring Harbor Laboratory Press, Cold Spring Harbor, New York.
4. McDonell, M. W., Simon, M. N., and Studier, F. W. (1977) *J. Mol. Biol.* 110, 119–146.
5. Southern, E. (1979) *Meth. Enzymol.* 68, 152–176.
6. Schwartz, D. C. and Cantor, C. R. (1984) *Cell* 37, 67–76.
7. Sanger, F., Nichlen, S. and Coulson, A. R. (1977) *Proc. Natl. Acad. Sci. U.S.A.* 75, 5463–5467.
8. Innis, M. A., Myambo, K. B., Gelfand, D. H., and Brow, M. A. D. (1988) *Proc. Natl. Acad. Sci. USA* 85, 9436–9440.
9. Orita, M., Iwahana, H., Kanazawa, H., Hayashi, K., and Sekiya, T. (1989) *Proc. Natl. Acad. Sci. USA* 86, 2766–2770.
10. Sarkar, G., Yoon, H. and Sommer, S. S. (1992) *Genomics* 13, 441–443.
11. Liu, Q. and Sommer, S. S. (1995) *BioTechniques* 18, 470–477.
12. Kuhn, R. and Hoffstetter-Kuhn, S. (1993) in Capillary Electrophoresis: Principles and Practice. pp. 37–101, Springer-Verlag, New York, New York.
13. Yoshitake, S., Schach, B. G., Foster, D. C., Davie, E. W., and Kurachi, K. (1985) *Biochemistry* 24, 3736–3750.
14. Sarkar, G. and Sommer, S. S. (1989) *Science* 244, 331–334.
15. Liu, Q. and Sommer, S. S. (1994) *PCR Methods and Applications* 4, 97–108.
16. Helling, R. B., Goodman, H. M., and Boyer, H. W. (1974) *J. Virol.* 14, 1235–1244.
17. Yarmola, E., Sokoloff, H. and Chramback, A. (1996) *Electrophoresis* 17, 1416–1419.
18. Good, N. E., Winget, G. D., Winter, W., Connolly, T. N., Izawa, S. and Singh, R. M. (1966) *Biochemistry* 5, 467–477.
19. Stoll, V. S. and Blanchard, J. S. (1990) *Methods Enzymol.* 182, 24–38.

20. Ellis, K. J. and Morrison, J. F. (1982) *Methods Enzymol.* 87, 405–26.
21. Ganguly, A., Rock, M. J. and Prockop, D. J. (1993) *Proc. Natl. Acad. Sci. U.S.A.* 90, 10325–10329.
22. Kohn, J. and Riches, P. G. (1978) *J. Immunol. Methods* 20, 325–331.
23. Ambler, J. and Rodgers, M. (1980) *Clin. Chem.* 26, 1221–23.
24. Liu, Q. and Sommer, S. S. (1998) *BioTechniques* 25, 50–56.
25. Kukita, Y., Tahira, T., Sommer, S. S., and Hayashi, K. (1997) *Hum. Mutat.* 10, 400–07.
26. Sasaki, T., Tian, H., Kukita, Y., Inazuka, M., Tahira, T., Imai, T., Yamauchi, M., Saito, T., Hori, T., Hashimoto-Tamaoki, T., Komatsu, K., Nikaido, O., and Hayashi, K. (1998) *Hum. Mutat.* 12, 186–195.
27. Orban, L., Tietz, D. and Chramback, A. (1987) *Electrophoresis* 8, 465–471.
28. Chramback, A. and Jovin, T. M. (1983) *Electrophoresis* 4, 190–200.

What is claimed is:

1. A pK-matched buffer comprising a weak acid and a weak base which have pKa values at 25° C. within about 0.3 units of one another, wherein the weak acid is TRICINE and the weak base is triethanolamine.

2. In an electrophoresis method, the improvement which comprises running the electrophoresis in a buffer of claim 1.

3. The method of claim 2, wherein the method is a gel electrophoresis method for separating nucleic acids or polypeptides.

* * * * *

UNITED STATES PATENT AND TRADEMARK OFFICE
CERTIFICATE OF CORRECTION

PATENT NO. : 6,582,574 B1  Page 1 of 1
DATED : June 24, 2003
INVENTOR(S) : Liu et al.

It is certified that error appears in the above-identified patent and that said Letters Patent is hereby corrected as shown below:

Column 1,
Line 7, after "March 31, 1999.," please delete "+gi."

Column 3,
Line 16, after "Life Technologies.," please replace "A" with -- $\lambda$ --.

Signed and Sealed this

Sixteenth Day of March, 2004

JON W. DUDAS
*Acting Director of the United States Patent and Trademark Office*